United States Patent
Yoneda et al.

(10) Patent No.: US 6,599,634 B2
(45) Date of Patent: Jul. 29, 2003

(54) FLUORINE-CONTAINING ORGANIC SILICON COMPOUND, WATER REPELLENT COMPOSITION CONTAINING IT, AND SURFACE-TREATED SUBSTRATE AND PROCESS FOR ITS PRODUCTION

(75) Inventors: Takashige Yoneda, Yokohama (JP); Tadashi Hamano, Aiko-gun (JP); Fumiaki Gunji, Aiko-gun (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 09/973,891

(22) Filed: Oct. 11, 2001

(65) Prior Publication Data

US 2002/0076563 A1 Jun. 20, 2002

(30) Foreign Application Priority Data

Oct. 12, 2000 (JP) ........................................ 2000-311829

(51) Int. Cl.$^7$ ................................................. B32B 9/04
(52) U.S. Cl. ........................ 428/447; 428/450; 428/429; 427/387; 427/393.4; 525/477; 528/12; 528/42; 106/287.27; 106/287.14; 556/454; 556/453; 556/450
(58) Field of Search ................................ 428/447, 429, 428/450; 427/387, 393.4; 525/477; 528/12, 42; 106/287.27, 287.14; 556/454, 457, 450

(56) References Cited

U.S. PATENT DOCUMENTS

| 5,834,612 A | 11/1998 | Furukawa et al. |
| 5,834,614 A | 11/1998 | Furukawa et al. |
| 5,976,702 A | 11/1999 | Yoneda et al. |
| 6,197,989 B1 | 3/2001 | Furukawa et al. |

OTHER PUBLICATIONS

Abstract, JP 03034988, Saho et al.*

* cited by examiner

*Primary Examiner*—Robert Dawson
*Assistant Examiner*—Christopher M. Keehan
(74) *Attorney, Agent, or Firm*—Oblon, Spivak, McClelland, Maier & Neustadt, P.C.

(57) ABSTRACT

A fluorine-containing organic silicon compound of the following formula (1):

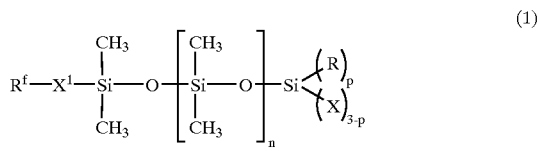

(1)

wherein $R^f$ is a fluorine-containing $C_{1-20}$ monovalent organic group, $X^1$ is an alkylene group, n is an integer of from 0 to 100, R is a $C_{1-5}$ monovalent hydrocarbon group, X is a hydrolyzable group, and p is 0, 1 or 2.

38 Claims, No Drawings

FLUORINE-CONTAINING ORGANIC SILICON COMPOUND, WATER REPELLENT COMPOSITION CONTAINING IT, AND SURFACE-TREATED SUBSTRATE AND PROCESS FOR ITS PRODUCTION

The present invention relates to a fluorine-containing organic silicon compound, a water repellent composition containing it, and a surface-treated substrate and a process for its production.

A fluorine-containing organic silicon compound has been applied to various industrial fields, since it is excellent in lubricating properties, water and oil repellency, oil and chemical resistance, etc. For example, when such a fluorine-containing organic silicon compound is used as a surface-treating agent or as an additive to a resin, the above-mentioned various properties can imparted to the surface of a substrate or a molded product of the resin.

On the other hand, various substrates having surface-treated layers are used in many fields. However, adverse effects of water to their surfaces have been problematic. For example, a front glass of an automobile, as an equipment for a transport, has a problem such that the transparency or see-through property decreases by e.g. deposition of raindrops, etc.

Further, such adverse effects brought by water are problematic not only to equipments for transports, but also to equipments to be used in various fields such as equipments for building construction and decoration or equipments for electric or electronic instruments.

Accordingly, it is strongly desired to impart a nature whereby waterdrops tend to hardly deposit on the surface of the substrate or deposited waterdrops can easily be removed (hereinafter referred to simply as a "waterdrop removal property"). In order to impart a waterdrop removal property to the surface, a surface treating agent for treating a substrate surface, has been proposed. For example, a silicone oil made of a silicone wax or an organopolysiloxane, or a surfactant, may be mentioned.

JP-A-7-252472 discloses a treating agent for water repellency containing a cohydrolyzate of a perfluoroalkyl group-containing organic silicon compound and a hydrolyzable group-containing methylpolysiloxane. However, when this treating agent for water repellency is coated on a substrate, before complete drying, the perfluoroalkyl group-containing organic silicon compound having a low surface energy, tends to move outside of the hydrolyzable group-containing methylpolysiloxane having a high surface energy, whereby a desired waterdrop falling property has not been obtained.

Further, conventional surface treatments required pre-treatment before coating, in many cases, and also had a problem such that coating irregularities were likely to occur during the coating. Further, the adhesion to the substrate of the treating agent itself was low, whereby the waterdrop removal property did not last in many cases, whereby the application was limited.

Further, it is desired that surface treatment can be applied not only to various substrates to be prepared anew in future but also to various substrates which are already in use. Namely, it is desired that a waterdrop removal property can be imparted simply by directly coating a surface-treating agent at room temperature. For example, when a front glass of an automobile in use is to be treated to have a waterdrop falling property imparted, it is practically impossible to replace the front glass or to carry out calcination after the surface treatment.

A first object of the present invention is to provide a novel fluorine-containing organic silicon compound which is useful as the main component of a water repellent composition.

A second object of the present invention is to provide a water repellent composition which contains such a novel fluorine-containing organic silicon compound as the main component and which, when coated on various substrates for surface treatment, is capable of imparting a waterdrop removal property to the substrate surface and provides excellent abrasion resistance, weather resistance, boiling resistance and chemical resistance, whereby the waterdrop removal property can be maintained for a long period of time.

A third object of the present invention is to provide a surface-treated substrate which has a waterdrop removal property and which is excellent in abrasion resistance, weather resistance, boiling resistance and chemical resistance, whereby such properties can be maintained semipermanently, and to provide a process for its production.

A fourth object of the present invention is to provide an equipment for transports, which has a waterdrop removal property and which is free from a problem such as deterioration of the function due to deposition of water, since such a property lasts for a long period of time.

The present inventors have found a novel fluorine-containing organic silicon compound and have found that a composition containing such a fluorine-containing organic silicon compound as the main component, is effective as a surface-treating agent which, when applied to various substrates, provides an excellent waterdrop removal property (a waterdrop falling property and water repellency) for a long period of time. Further, they have found that such surface treatment can be easily carried out, and various substrates having the surface treatment applied, are very useful as surface-treated substrates having a waterdrop removal property, particularly as equipments for transports. The present invention has been accomplished on the basis of these discoveries.

Namely, the present invention provides a fluorine-containing organic silicon compound of the following formula (1):

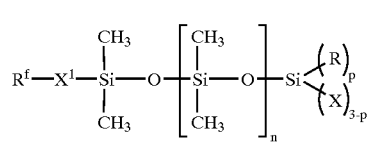

wherein $R^f$ is a fluorine-containing $C_{1-20}$ monovalent organic group, $X^1$ is an alkylene group, n is an integer of from 0 to 100, R is a $C_{1-5}$ monovalent hydrocarbon group, X is a hydrolyzable group, and p is 0, 1 or 2.

$R^f$ is preferably a monovalent polyfluorohydrocarbon group. The "monovalent polyfluorohydrocarbon group" is a group having at least two hydrogen atoms in a monovalent hydrocarbon group substituted by fluorine atoms. The carbon number of $R^f$ is from 1 to 20, preferably from 4 to 16, particularly preferably from 4 to 12. $R^f$ is preferably a polyfluoroalkyl group.

The number of fluorine atoms in $R^f$ is preferably at least 60%, particularly preferably at least 80%, as represented by (the number of fluorine atoms in the polyfluorohydrocarbon group)/(the number of hydrogen atoms in the corresponding hydrocarbon group having the same carbon number as the polyfluorohydrocarbon group)×100(%). $R^f$ is preferably a perfluorohydrocarbon group (a group having all of hydrogen atoms in a hydrocarbon group substituted by fluorine atoms), particularly preferably a perfluoroalkyl group.

The structure of $R^f$ may be a linear structure or a branched structure, but a linear structure is preferred.

In the case of a branched structure, it is preferred that the branched portion is a short chain having a carbon number of from about 1 to 3, and the branched portion is located in the vicinity of a terminal of $R^f$.

Specific examples of $R^f$ will be given below. The following examples include structural isomeric groups having the same molecular formulae. Here, s is an integer of from 1 to 17.

$C_4F_9$— (such as $F(CF_2)_4$—, $(CF_3)_2CFCF_2$—, $(CF_3)_3C$—, or $CF_3CF_2CF(CF_3)$—), $C_5F_{11}$— (such as $F(CF_2)_5$—, $(CF_3)_2CF(CF_2)_2$—, $(CF_3)_3CCF_2$—, or $CF_3(CF_2)_2CF(CF_3)$—), $C_6F_{13}$—, $C_8F_{17}$—, $C_{10}F_{21}$—, $C_{12}F_{25}$—, $C_{14}F_{29}$—, $C_{16}F_{33}$—, $C_{18}F_{37}$—, $C_{20}F_{41}$—, and $(CF_3)_2CF(CF_2)_s$—.

$X^1$ is preferably —$(CH_2)_a$— (wherein a is an integer of at least 2), and a is preferably an integer of from 2 to 6, particularly preferably 2 or 3. Namely, $X^1$ is particularly preferably —$CH_2CH_2$— or —$CH_2CH_2CH_2$—. n is an integer of from 0 to 100, preferably from 1 to 50, particularly preferably from 2 to 30.

R is a $C_{1-5}$ monovalent hydrocarbon group. R is preferably a $C_{1-5}$ alkyl group, such as a methyl group, an ethyl group, a n-propyl group, an isopropyl group, a n-butyl group, an isobutyl group or a s-butyl group.

X is a hydrolyzable group and may, for example, be preferably $OR^a$ (wherein $R^a$ is a $C_{1-6}$ monovalent hydrocarbon group), a chlorine atom, NCO or an acyloxy group. $OR^a$ may, for example, be preferably a methoxy group, an ethoxy group, a n-propoxy group, an isopropoxy group, an isopropenoxy group, a n-butoxy group, or an acetoxy group.

A p number of R's may be the same or different, and a (3-p) number of X's may be the same or different.

Symbol p is 0, 1 or 2, and in the production of a surface-treated substrate, as described hereinafter, p is preferably 0 or 1 from the viewpoint of the adhesion to the first layer and the second layer.

The following compounds may be mentioned as specific preferred examples of the fluorine-containing organic silicon compound of the present invention. The following specific examples include structural isomeric groups.

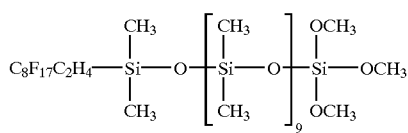
(a-1)

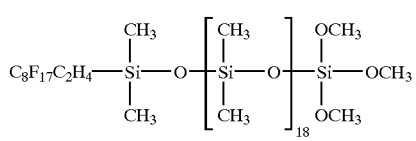
(a-2)

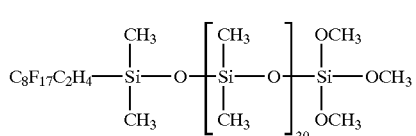
(a-3)

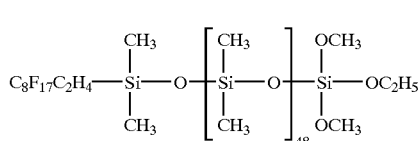
(a-4)

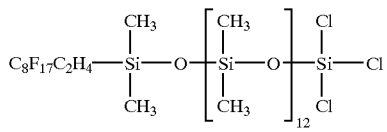
(a-5)

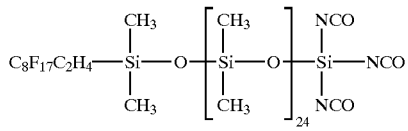
(a-6)

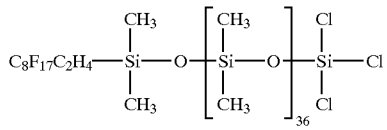
(a-13)

The fluorine-containing organic silicon compound of the present invention may be prepared, for example, by a process which comprises reacting a fluorine-containing alkyldimethylsilanol with hexamethylcyclotrisiloxane by living polymerization in the presence of an alkyl lithium compound, and then reacting a hydrolyzable group-containing chlorosilane thereto.

The water repellent composition of the present invention may contain one or more fluorine-containing organic silicon compounds of the above formula (1).

The water-repellent composition is one containing the above fluorine-containing organic silicon compound as the main component, and it may contain the fluorine-containing organic silicon compound alone, or it may contain the fluorine-containing organic silicon compound together with another component. It preferably contains, as such another component, a fluorine-containing reactive silane compound (II) and/or a no fluorine-containing reactive silane compound (III) having an angle of contact with water of at least 100°. Further, the water repellent composition may contain a solvent.

The fluorine-containing reactive silane compound (II) is a reactive silane compound having a fluorine-containing organic group and is a compound capable of forming a surface having an angle of contact with water of at least 100°. Here, "a compound capable of forming a surface having an angle of contact with water of at least 100°" is a compound such that when the surface of a substrate is treated with the compound so that the surface is completely covered with the compound so as not to be exposed, the surface after the treatment has an angle of contact with water of at least 100°.

The compound (II) has a structure wherein reactive groups are directly bonded to silicon atoms. As such a reactive group, an isocyanate group, a halogen atom, an alkoxy group, an acyloxy group, an alkoxy-substituted alkoxy group, an aminoxy group, an amide group, an acid amide group or a ketoximate group, may, for example, be mentioned. Among them, a $C_{1-4}$ alkoxy group, an acyloxy group, an isocyanate group or a chlorine atom, is preferred. From the viewpoint of the bonding property to the surface-treated layer or the substrate, it is preferred that two or more reactive groups are bonded to one silicon atom.

It is considered that by the reactivity of such reactive groups, the compound (II) provides excellent properties such as the waterdrop removal property, the abrasion resistance, the chemical resistance and the weather resistance. Further, as described hereinafter, by selecting the organic group, these properties can further be improved.

The compound (II) may be used as it is, or it may be used in the form of a hydrolyzable product. A hydrolyzable product of the compound (II) is a compound having e.g. silanol groups formed by hydrolysis of some or all of the reactive groups of the compound (II) in water, an acidic aqueous solution or an alkaline aqueous solution, or a compound having two or more molecules condensed by the reaction of such silanol groups. As the acidic aqueous solution, an aqueous solution of e.g. hydrochloric acid, acetic acid, sulfuric acid, phosphoric acid, sulfonic acid or methanesulfonic acid, may be employed.

The compound (II) is preferably at least one member selected from compounds of the following formulae (IIA) or (IIB) (hereinafter referred to also as compounds (IIA) and (IIB)):

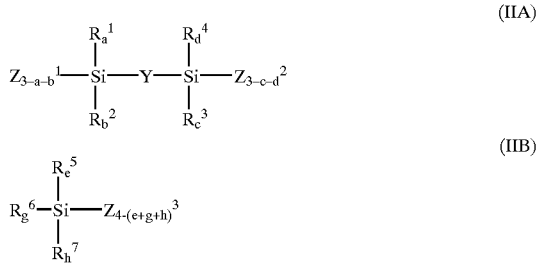

In the formula (IIA), each of $R^1$, $R^2$, $R^3$ and $R^4$ is a hydrogen atom or a $C_{1-21}$ monovalent organic group, Y is a bivalent organic group, provided that at least one of $R^1$, $R^2$, $R^3$, $R^4$ and Y is a fluorine-containing organic group, and each of $Z^1$ and $Z^2$ is an isocyanate group or a hydrolyzable group, each of a and b is 0, 1 or 2, provided $0 \leq a+b \leq 2$, and each of c and d is 0, 1 or 2, provided $0 \leq c+d \leq 2$.

A (3-a-b) number of $Z^1$'s and a (3-c-d) number of $Z^2$'s may be the same or different.

From the viewpoint of the adhesion to the first layer and to the after-mentioned third layer or the substrate, each of a and b is preferably 1 or less, more preferably 0. For the same reason, each of c and d is preferably 0.

In the formula (IIB), each of $R^5$, $R^6$ and $R^7$ is a hydrogen atom or a $C_{1-21}$ monovalent organic group, provided that at least one of $R^5$, $R^6$ and $R^7$ is a fluorine-containing organic group, $Z^3$ is an isocyanate group or a hydrolyzable group, and each of e, g and h is 0, 1 or 2, provided $1 \leq (e+g+h) \leq 3$. An e number of $R^5$'s, a g number of $R^6$'s and a h number of $R^7$'s may be the same or different. At least one of an e number of $R^5$'s, a g number of $R^6$'s and a h number of $R^7$'s is a fluorine-containing organic group.

The fluorine-containing organic group is preferably one wherein a carbon atom having no fluorine atoms (such as a carbon atom of a methylene group, an ethylene group or a propylene group) is bonded to a silicon atom.

When Y is a bivalent fluorine-containing organic group, Y is preferably a polyfluoroalkylene group, a polyfluorooxyalkylene group (one wherein at least one ether bond is present in the carbon chain of the alkylene group), or a polyfluorothioxane alkylene group (one wherein at least one thioether bond is present in the carbon chain of the alkylene group). Particularly preferred is one wherein moieties bonded to silicon atoms at both sides are polymethylene groups, particularly dimethylene groups) and the intermediate moiety is a perfluoroalkylene group or a perfluorooxyalkylene group. In such a case, the carbon number of Y is preferably from 2 to 30, more preferably from 4 to 16.

When Y is not a bivalent fluorine-containing organic group, it is preferably an alkylene group, an oxyalkylene group or a thioxaalkylene group. In such a case, the carbon number of Y is preferably from 2 to 30, more preferably from 2 to 12.

In a case where any one of an a number of $R^1$'s and a b number of $R^2$'s is a monovalent fluorine-containing organic group and in a case where any one of a c number of $R^3$'s and a d number of $R^4$'s is a monovalent fluorine-containing organic group, such an organic group is preferably a polyfluoroalkyl group, a polyfluorooxaalkyl group or a polyfluorothioxaalkyl group. Or, it is preferably an organic group wherein any one of such groups and a hydrocarbon group such as an alkylene group, are bonded by a connecting bond such as an ester bond, an ether bond, a thioether bond, an imino bond, an amide bond, an urethane bond or other bond. The polyfluoroalkyl group and the polyfluorooxaalkyl group are preferably such that the terminal bonded to a silicon atom or the vicinity thereof is an alkylene group (particularly a dimethylene group), and other portion is a perfluoroalkylene group or the like. Particularly preferred is a perfluoroalkyl group having at least 3 carbon atoms, a perfluorooxaalkyl group having at least 3 carbon atoms, or a perfluorothioxaalkyl group having at least 3 carbon atoms. Especially preferred is a perfluoroalkyl group having from 3 to 16 carbon atoms.

In a case where an organic group having no fluorine atom, is present in the compound (IIA) and the compound (IIB), such an organic group is preferably a hydrocarbon group such as an alkyl group, an alkenyl group, a cycloalkyl group or an aryl group; a halogenated hydrocarbon group such as a chloroalkyl group; a (halogenated)hydrocarbon group having a hydroxyl group, an epoxy group, an amino group, a mercapto group, a carboxy group or other functional group; or a (halogenated)hydrocarbon group having in its carbon chain, an ester bond, an ether bond, a thioether bond, an imino bond, an amide bond, a urethane bond or other connecting bond. Among them, a methyl group or a long chain hydrocarbon group is preferred. As the long chain hydrocarbon group, a $C_{4-20}$ alkyl group is preferred.

Now, specific examples of the compound (IIA) and the compound (IIB) will be shown below. In the following formulae, $R^x$ represents a $C_{3-16}$ polyfluoroalkyl group, and other symbols have the same meanings as mentioned above.

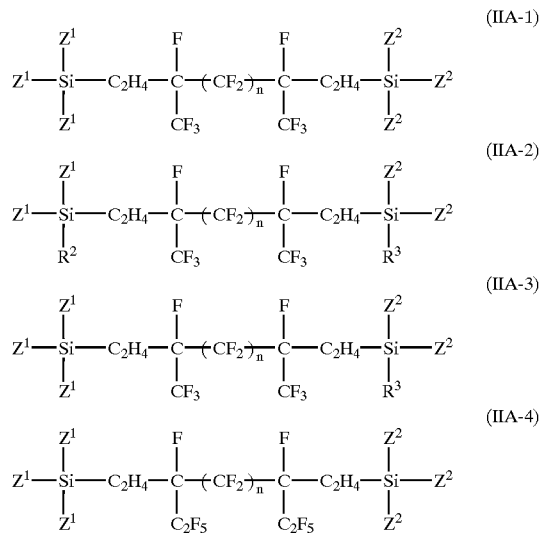

-continued $$\text{(IIA-5)} \quad Z^1-\underset{R^2}{\underset{|}{Si}}-C_2H_4-\underset{C_2F_5}{\underset{|}{C}}-(CF_2)_n-\underset{C_2F_5}{\underset{|}{C}}-C_2H_4-\underset{R^3}{\underset{|}{Si}}-Z^2$$

$$\text{(IIA-6)} \quad Z^1-\underset{Z^1}{\underset{|}{Si}}-C_2H_4-\underset{C_2F_5}{\underset{|}{C}}-(CF_2)_n-\underset{C_2F_5}{\underset{|}{C}}-C_2H_4-\underset{R^3}{\underset{|}{Si}}-Z^2$$

$$\text{(IIA-7)} \quad Z^1-\underset{Z^1}{\underset{|}{Si}}-C_2H_4-\underset{CF_3}{\underset{|}{C}}-CF_2-O-(CF_2)_n-O-CF_2-\underset{CF_3}{\underset{|}{C}}-C_2H_4-\underset{Z^1}{\underset{|}{Si}}-Z^2$$

$$\text{(IIA-8)} \quad Z^1-\underset{R^2}{\underset{|}{Si}}-C_2H_4-\underset{CF_3}{\underset{|}{C}}-CF_2-O-(CF_2)_n-O-CF_2-\underset{CF_3}{\underset{|}{C}}-C_2H_4-\underset{R^3}{\underset{|}{Si}}-Z^2$$

$$\text{(IIA-9)} \quad Z^1-\underset{Z^1}{\underset{|}{Si}}-C_2H_4-\underset{CF_3}{\underset{|}{C}}-CF_2-O-(CF_2)_n-O-CF_2-\underset{CF_3}{\underset{|}{C}}-C_2H_4-\underset{R^3}{\underset{|}{Si}}-Z^2$$

$$\text{(IIA-10)} \quad Z^1-\underset{Z^1}{\underset{|}{Si}}-C_2H_4-(CF_2)_n-C_2H_4-\underset{Z^1}{\underset{|}{Si}}-Z^2$$

$$\text{(IIA-11)} \quad Z^1-\underset{R^2}{\underset{|}{Si}}-C_2H_4-(CF_2)_n-C_2H_4-\underset{R^3}{\underset{|}{Si}}-Z^2$$

$$\text{(IIA-12)} \quad Z^1-\underset{Z^1}{\underset{|}{Si}}-C_2H_4-(CF_2)_n-C_2H_4-\underset{R^3}{\underset{|}{Si}}-Z^2$$

$$\text{(IIA-13)} \quad Z^1-\underset{R^x}{\underset{|}{Si}}-C_2H_4-\underset{CF_3}{\underset{|}{C}}-(CF_2)_n-\underset{CF_3}{\underset{|}{C}}-C_2H_4-\underset{R^x}{\underset{|}{Si}}-Z^2$$

$$\text{(IIA-14)} \quad Z^1-\underset{R^2}{\underset{|}{Si}}-C_2H_4-\underset{CF_3}{\underset{|}{C}}-(CF_2)_n-\underset{CF_3}{\underset{|}{C}}-C_2H_4-\underset{R^x}{\underset{|}{Si}}-Z^2$$

$$\text{(IIA-15)} \quad Z^1-\underset{R^x}{\underset{|}{Si}}-C_2H_4-\underset{C_2F_5}{\underset{|}{C}}-(CF_2)_n-\underset{C_2F_5}{\underset{|}{C}}-C_2H_4-\underset{R^x}{\underset{|}{Si}}-Z^2$$

$$\text{(IIA-16)} \quad Z^1-\underset{R^2}{\underset{|}{Si}}-C_2H_4-\underset{C_2F_5}{\underset{|}{C}}-(CF_2)_n-\underset{C_2F_5}{\underset{|}{C}}-C_2H_4-\underset{R^3}{\underset{|}{Si}}-Z^2$$

-continued $$\text{(IIA-17)} \quad Z^1-\underset{Z^1}{\underset{|}{Si}}-C_2H_4-\underset{CF_3}{\underset{|}{C}}-CF_2-O-(CF_2)_n-O-CF_2-\underset{CF_3}{\underset{|}{C}}-C_2H_4-\underset{R^x}{\underset{|}{Si}}-Z^2$$

$$\text{(IIA-18)} \quad Z^1-\underset{R^2}{\underset{|}{Si}}-C_2H_4-\underset{CF_3}{\underset{|}{C}}-CF_2-O-(CF_2)_n-O-CF_2-\underset{CF_3}{\underset{|}{C}}-C_2H_4-\underset{R^3}{\underset{|}{Si}}-Z^2$$

$$\text{(IIA-19)} \quad Z^1-\underset{Z^1}{\underset{|}{Si}}-C_2H_4-(CF_2)_n-C_2H_4-\underset{Z^2}{\underset{|}{Si}}-Z^2$$

$$\text{(IIA-20)} \quad Z^1-\underset{R^2}{\underset{|}{Si}}-C_2H_4-(CF_2)_n-C_2H_4-\underset{R^3}{\underset{|}{Si}}-Z^2$$

$$\text{(IIA-21)} \quad Z^1-\underset{Z^1}{\underset{|}{Si}}-C_2H_4-\underset{CF_3}{\underset{|}{C}}-(CF_2)_n-\underset{CF_3}{\underset{|}{C}}-C_2H_4-\underset{Z^2}{\underset{|}{Si}}-Z^2$$

$$\text{(IIA-22)} \quad Z^1-\underset{R^2}{\underset{|}{Si}}-C_2H_4-\underset{CF_3}{\underset{|}{C}}-(CF_2)_n-\underset{CF_3}{\underset{|}{C}}-C_2H_4-\underset{R^3}{\underset{|}{Si}}-Z^2$$

$$\text{(IIA-23)} \quad Z^1-\underset{Z^1}{\underset{|}{Si}}-C_2H_4-\underset{C_2F_5}{\underset{|}{C}}-(CF_2)_n-\underset{C_2F_5}{\underset{|}{C}}-C_2H_4-\underset{R^x}{\underset{|}{Si}}-Z^2$$

$$\text{(IIA-24)} \quad Z^1-\underset{R^2}{\underset{|}{Si}}-C_2H_4-\underset{C_2F_5}{\underset{|}{C}}-(CF_2)_n-\underset{C_2F_5}{\underset{|}{C}}-C_2H_4-\underset{R^3}{\underset{|}{Si}}-Z^2$$

$$\text{(IIA-25)} \quad Z^1-\underset{R^2}{\underset{|}{Si}}-C_2H_4-\underset{CF_3}{\underset{|}{C}}-(CF_2)_n-\underset{CF_3}{\underset{|}{C}}-C_2H_4-\underset{R^x}{\underset{|}{Si}}-Z^2$$

$$\text{(IIA-26)} \quad Z^1-\underset{Z^1}{\underset{|}{Si}}-C_2H_4-\underset{CF_3}{\underset{|}{C}}-CF_2-O-(CF_2)_n-O-CF_2-\underset{CF_3}{\underset{|}{C}}-C_2H_4-\underset{R^x}{\underset{|}{Si}}-Z^2$$

$$\text{(IIA-27)} \quad Z^1-\underset{R^2}{\underset{|}{Si}}-C_2H_4-\underset{CF_3}{\underset{|}{C}}-CF_2-O-(CF_2)_n-O-CF_2-\underset{CF_3}{\underset{|}{C}}-C_2H_4-\underset{R^3}{\underset{|}{Si}}-Z^2$$

$$\text{(IIA-28)} \quad Z^1-\underset{Z^1}{\underset{|}{Si}}-C_2H_4-(CF_2)_n-C_2H_4-\underset{Z^2}{\underset{|}{Si}}-Z^2$$

(IIA-29)
$$Z^1-\underset{\underset{R^2}{|}}{\overset{\overset{Z^1}{|}}{Si}}-C_2H_4-(CF_2)_n-C_2H_4-\underset{\underset{R^3}{|}}{\overset{\overset{R^x}{|}}{Si}}-Z^2$$

(IIA-30)
$$Z^1-\underset{\underset{Z^1}{|}}{\overset{\overset{Z^1}{|}}{Si}}-C_2H_4-\underset{\underset{CF_3}{|}}{\overset{\overset{F}{|}}{C}}-(CF_2)_n-\underset{\underset{CF_3}{|}}{\overset{\overset{F}{|}}{C}}-C_2H_4-\underset{\underset{R^3}{|}}{\overset{\overset{R^x}{|}}{Si}}-Z^2$$

(IIA-31)
$$Z^1-\underset{\underset{R^2}{|}}{\overset{\overset{Z^1}{|}}{Si}}-C_2H_4-\underset{\underset{CF_3}{|}}{\overset{\overset{F}{|}}{C}}-(CF_2)_n-\underset{\underset{CF_3}{|}}{\overset{\overset{F}{|}}{C}}-C_2H_4-\underset{\underset{Z^2}{|}}{\overset{\overset{R^x}{|}}{Si}}-Z^2$$

(IIA-32)
$$Z^1-\underset{\underset{Z^1}{|}}{\overset{\overset{Z^1}{|}}{Si}}-C_2H_4-\underset{\underset{C_2F_5}{|}}{\overset{\overset{F}{|}}{C}}-(CF_2)_n-\underset{\underset{C_2F_5}{|}}{\overset{\overset{F}{|}}{C}}-C_2H_4-\underset{\underset{R^x}{|}}{\overset{\overset{R^3}{|}}{Si}}-Z^2$$

(IIA-33)
$$Z^1-\underset{\underset{R^2}{|}}{\overset{\overset{Z^1}{|}}{Si}}-C_2H_4-\underset{\underset{C_2F_5}{|}}{\overset{\overset{F}{|}}{C}}-(CF_2)_n-\underset{\underset{C_2F_5}{|}}{\overset{\overset{F}{|}}{C}}-C_2H_4-\underset{\underset{Z^2}{|}}{\overset{\overset{R^x}{|}}{Si}}-Z^2$$

(IIA-34)
$$Z^1-\underset{\underset{Z^1}{|}}{\overset{\overset{Z^1}{|}}{Si}}-C_2H_4-\underset{\underset{CF_3}{|}}{\overset{\overset{F}{|}}{C}}-CF_2-O-(CF_2)_n-O-CF_2-\underset{\underset{CF_3}{|}}{\overset{\overset{F}{|}}{C}}-C_2H_4-\underset{\underset{R^3}{|}}{\overset{\overset{R^x}{|}}{Si}}-Z^2$$

(IIA-35)
$$Z^1-\underset{\underset{R^2}{|}}{\overset{\overset{Z^1}{|}}{Si}}-C_2H_4-\underset{\underset{CF_3}{|}}{\overset{\overset{F}{|}}{C}}-CF_2-O-(CF_2)_n-O-CF_2-\underset{\underset{CF_3}{|}}{\overset{\overset{F}{|}}{C}}-C_2H_4-\underset{\underset{Z^2}{|}}{\overset{\overset{R^x}{|}}{Si}}-Z^2$$

(IIA-36)
$$Z^1-\underset{\underset{Z^1}{|}}{\overset{\overset{Z^1}{|}}{Si}}-C_2H_4-(CF_2)_n-C_2H_4-\underset{\underset{R^3}{|}}{\overset{\overset{R^x}{|}}{Si}}-Z^2$$

(IIA-37)
$$Z^1-\underset{\underset{R^2}{|}}{\overset{\overset{Z^1}{|}}{Si}}-C_2H_4-(CF_2)_n-C_2H_4-\underset{\underset{Z^2}{|}}{\overset{\overset{R^x}{|}}{Si}}-Z^2$$

(IIA-38)
$$Z^1-\underset{\underset{R^x}{|}}{\overset{\overset{Z^1}{|}}{Si}}-C_2H_4-\underset{\underset{R^x}{|}}{\overset{\overset{Z^2}{|}}{Si}}-Z^2$$

(IIA-39)
$$Z^1-\underset{\underset{R^x}{|}}{\overset{\overset{Z^1}{|}}{Si}}-C_2H_4-\underset{\underset{Z^2}{|}}{\overset{\overset{Z^2}{|}}{Si}}-Z^2$$

(IIA-40)
$$Z^1-\underset{\underset{R^x}{|}}{\overset{\overset{R^2}{|}}{Si}}-C_2H_4-\underset{\underset{Z^2}{|}}{\overset{\overset{Z^2}{|}}{Si}}-Z^2$$

(IIA-41)
$$Z^1-\underset{\underset{R^x}{|}}{\overset{\overset{R^2}{|}}{Si}}-C_2H_4-\underset{\underset{Z^2}{|}}{\overset{\overset{R^3}{|}}{Si}}-Z^2$$

(IIA-42)
$$Z^1-\underset{\underset{R^x}{|}}{\overset{\overset{Z^1}{|}}{Si}}-C_2H_4-\underset{\underset{Z^2}{|}}{\overset{\overset{R^3}{|}}{Si}}-Z^2$$

(IIA-43)
$$Z^1-\underset{\underset{R^2}{|}}{\overset{\overset{R^x}{|}}{Si}}-C_2H_4-\underset{\underset{R^3}{|}}{\overset{\overset{R^x}{|}}{Si}}-Z^2$$

(IIA-44)
$$Z^1-\underset{\underset{R^2}{|}}{\overset{\overset{R^x}{|}}{Si}}-C_2H_4-\underset{\underset{Z^2}{|}}{\overset{\overset{R^x}{|}}{Si}}-Z^2$$

(IIA-45)
$$Z^1-\underset{\underset{R^x}{|}}{\overset{\overset{Z^1}{|}}{Si}}-C_2H_4-O-C_2H_4-\underset{\underset{R^x}{|}}{\overset{\overset{Z^2}{|}}{Si}}-Z^2$$

(IIA-46)
$$Z^1-\underset{\underset{R^x}{|}}{\overset{\overset{Z^1}{|}}{Si}}-C_2H_4-O-C_2H_4-\underset{\underset{Z^2}{|}}{\overset{\overset{Z^2}{|}}{Si}}-Z^2$$

(IIA-47)
$$Z^1-\underset{\underset{R^x}{|}}{\overset{\overset{R^2}{|}}{Si}}-C_2H_4-O-C_2H_4-\underset{\underset{Z^2}{|}}{\overset{\overset{Z^2}{|}}{Si}}-Z^2$$

(IIA-48)
$$Z^1-\underset{\underset{R^x}{|}}{\overset{\overset{R^2}{|}}{Si}}-C_2H_4-O-C_2H_4-\underset{\underset{Z^2}{|}}{\overset{\overset{R^3}{|}}{Si}}-Z^2$$

(IIA-49)
$$Z^1-\underset{\underset{R^x}{|}}{\overset{\overset{Z^1}{|}}{Si}}-C_2H_4-O-C_2H_4-\underset{\underset{Z^2}{|}}{\overset{\overset{R^3}{|}}{Si}}-Z^2$$

(IIA-50)
$$Z^1-\underset{\underset{R^2}{|}}{\overset{\overset{R^x}{|}}{Si}}-C_2H_4-O-C_2H_4-\underset{\underset{R^3}{|}}{\overset{\overset{R^x}{|}}{Si}}-Z^2$$

(IIA-51)
$$Z^1-\underset{\underset{R^2}{|}}{\overset{\overset{R^x}{|}}{Si}}-C_2H_4-O-C_2H_4-\underset{\underset{Z^2}{|}}{\overset{\overset{R^x}{|}}{Si}}-Z^2$$

(IIA-52)
$$Z^1-\underset{\underset{R^x}{|}}{\overset{\overset{Z^1}{|}}{Si}}-C_2H_4-S-C_2H_4-\underset{\underset{R^x}{|}}{\overset{\overset{Z^2}{|}}{Si}}-Z^2$$

(IIA-53)
$$Z^1-\underset{\underset{R^x}{|}}{\overset{\overset{Z^1}{|}}{Si}}-C_2H_4-S-C_2H_4-\underset{\underset{Z^2}{|}}{\overset{\overset{Z^2}{|}}{Si}}-Z^2$$

(IIA-54)
$$Z^1-\underset{\underset{R^x}{|}}{\overset{\overset{R^2}{|}}{Si}}-C_2H_4-S-C_2H_4-\underset{\underset{Z^2}{|}}{\overset{\overset{Z^2}{|}}{Si}}-Z^2$$

$$Z^1-\underset{\underset{R^x}{|}}{\overset{\overset{R^2}{|}}{Si}}-C_2H_4-S-C_2H_4-\underset{\underset{Z^2}{|}}{\overset{\overset{R^3}{|}}{Si}}-Z^2 \quad \text{(IIA-55)}$$

$$Z^1-\underset{\underset{R^x}{|}}{\overset{\overset{Z^1}{|}}{Si}}-C_2H_4-S-C_2H_4-\underset{\underset{Z^2}{|}}{\overset{\overset{R^3}{|}}{Si}}-Z^2 \quad \text{(IIA-56)}$$

$$Z^1-\underset{\underset{R^2}{|}}{\overset{\overset{R^x}{|}}{Si}}-C_2H_4-S-C_2H_4-\underset{\underset{R^3}{|}}{\overset{\overset{R^x}{|}}{Si}}-Z^2 \quad \text{(IIA-57)}$$

$$Z^1-\underset{\underset{R^2}{|}}{\overset{\overset{R^x}{|}}{Si}}-C_2H_4-S-C_2H_4-\underset{\underset{Z^2}{|}}{\overset{\overset{R^x}{|}}{Si}}-Z^2 \quad \text{(IIA-58)}$$

$$Z^1-\underset{\underset{R^x}{|}}{\overset{\overset{Z^1}{|}}{Si}}-C_2H_4-O-C_2H_4-O-C_2H_4-\underset{\underset{R^x}{|}}{\overset{\overset{Z^2}{|}}{Si}}-Z^2 \quad \text{(IIA-59)}$$

$$Z^1-\underset{\underset{R^x}{|}}{\overset{\overset{Z^1}{|}}{Si}}-C_2H_4-O-C_2H_4-O-C_2H_4-\underset{\underset{Z^2}{|}}{\overset{\overset{Z^2}{|}}{Si}}-Z^2 \quad \text{(IIA-60)}$$

$$Z^1-\underset{\underset{R^x}{|}}{\overset{\overset{R^2}{|}}{Si}}-C_2H_4-O-C_2H_4-O-C_2H_4-\underset{\underset{Z^2}{|}}{\overset{\overset{Z^2}{|}}{Si}}-Z^2 \quad \text{(IIA-61)}$$

$$Z^1-\underset{\underset{R^x}{|}}{\overset{\overset{R^2}{|}}{Si}}-C_2H_4-O-C_2H_4-O-C_2H_4-\underset{\underset{Z^2}{|}}{\overset{\overset{R^3}{|}}{Si}}-Z^2 \quad \text{(IIA-62)}$$

$$Z^1-\underset{\underset{R^x}{|}}{\overset{\overset{Z^1}{|}}{Si}}-C_2H_4-O-C_2H_4-O-C_2H_4-\underset{\underset{Z^2}{|}}{\overset{\overset{R^3}{|}}{Si}}-Z^2 \quad \text{(IIA-63)}$$

$$Z^1-\underset{\underset{R^2}{|}}{\overset{\overset{R^x}{|}}{Si}}-C_2H_4-O-C_2H_4-O-C_2H_4-\underset{\underset{R^3}{|}}{\overset{\overset{R^x}{|}}{Si}}-Z^2 \quad \text{(IIA-64)}$$

$$Z^1-\underset{\underset{R^2}{|}}{\overset{\overset{R^x}{|}}{Si}}-C_2H_4-O-C_2H_4-O-C_2H_4-\underset{\underset{Z^2}{|}}{\overset{\overset{R^x}{|}}{Si}}-Z^2 \quad \text{(IIA-65)}$$

$$Z^1-\underset{\underset{R^x}{|}}{\overset{\overset{Z^1}{|}}{Si}}-C_2H_4-S-C_2H_4-S-C_2H_4-\underset{\underset{R^x}{|}}{\overset{\overset{Z^2}{|}}{Si}}-Z^2 \quad \text{(IIA-66)}$$

$$Z^1-\underset{\underset{R^x}{|}}{\overset{\overset{Z^1}{|}}{Si}}-C_2H_4-S-C_2H_4-S-C_2H_4-\underset{\underset{Z^2}{|}}{\overset{\overset{Z^2}{|}}{Si}}-Z^2 \quad \text{(IIA-67)}$$

$$Z^1-\underset{\underset{R^x}{|}}{\overset{\overset{R^2}{|}}{Si}}-C_2H_4-S-C_2H_4-S-C_2H_4-\underset{\underset{Z^2}{|}}{\overset{\overset{Z^2}{|}}{Si}}-Z^2 \quad \text{(IIA-68)}$$

$$Z^1-\underset{\underset{R^x}{|}}{\overset{\overset{R^2}{|}}{Si}}-C_2H_4-S-C_2H_4-S-C_2H_4-\underset{\underset{Z^2}{|}}{\overset{\overset{R^3}{|}}{Si}}-Z^2 \quad \text{(IIA-69)}$$

$$Z^1-\underset{\underset{R^x}{|}}{\overset{\overset{Z^1}{|}}{Si}}-C_2H_4-S-C_2H_4-S-C_2H_4-\underset{\underset{Z^2}{|}}{\overset{\overset{R^3}{|}}{Si}}-Z^2 \quad \text{(IIA-70)}$$

$$Z^1-\underset{\underset{R^2}{|}}{\overset{\overset{R^x}{|}}{Si}}-C_2H_4-S-C_2H_4-S-C_2H_4-\underset{\underset{R^3}{|}}{\overset{\overset{R^x}{|}}{Si}}-Z^2 \quad \text{(IIA-71)}$$

$$Z^1-\underset{\underset{R^2}{|}}{\overset{\overset{R^x}{|}}{Si}}-C_2H_4-S-C_2H_4-S-C_2H_4-\underset{\underset{Z^2}{|}}{\overset{\overset{R^x}{|}}{Si}}-Z^2 \quad \text{(IIA-72)}$$

$$R^x-C_2H_4-\underset{\underset{Z^3}{|}}{\overset{\overset{Z^3}{|}}{Si}}-Z^3 \quad \text{(IIB-1)}$$

$$R^x-C_2H_4-\underset{\underset{R^5}{|}}{\overset{\overset{Z^3}{|}}{Si}}-Z^3 \quad \text{(IIB-2)}$$

$$R^x-C_2H_4-\underset{\underset{C_2H_4-R^x}{|}}{\overset{\overset{Z^3}{|}}{Si}}-Z^3 \quad \text{(IIB-3)}$$

$$R^x-C_2H_4-\underset{\underset{C_2H_4-R^x}{|}}{\overset{\overset{Z^3}{|}}{Si}}-C_2H_4-R^x \quad \text{(IIB-4)}$$

$$R^x-\overset{\overset{O}{\|}}{C}-\overset{\overset{H}{|}}{N}-C_3H_6-\underset{\underset{Z^3}{|}}{\overset{\overset{Z^3}{|}}{Si}}-Z^3 \quad \text{(IIB-5)}$$

$$R^x-\overset{\overset{O}{\|}}{C}-\overset{\overset{H}{|}}{N}-C_3H_6-\underset{\underset{R^5}{|}}{\overset{\overset{Z^3}{|}}{Si}}-Z^3 \quad \text{(IIB-6)}$$

$$R^x-\overset{\overset{O}{\|}}{C}-\overset{\overset{H}{|}}{N}-C_2H_4-\overset{\overset{H}{|}}{N}-C_3H_6-\underset{\underset{Z^3}{|}}{\overset{\overset{Z^3}{|}}{Si}}-Z^3 \quad \text{(IIB-7)}$$

$$R^x-\overset{\overset{O}{\|}}{C}-\overset{\overset{H}{|}}{N}-C_2H_4-\overset{\overset{H}{|}}{N}-C_3H_6-\underset{\underset{R^5}{|}}{\overset{\overset{Z^3}{|}}{Si}}-Z^3 \quad \text{(IIB-8)}$$

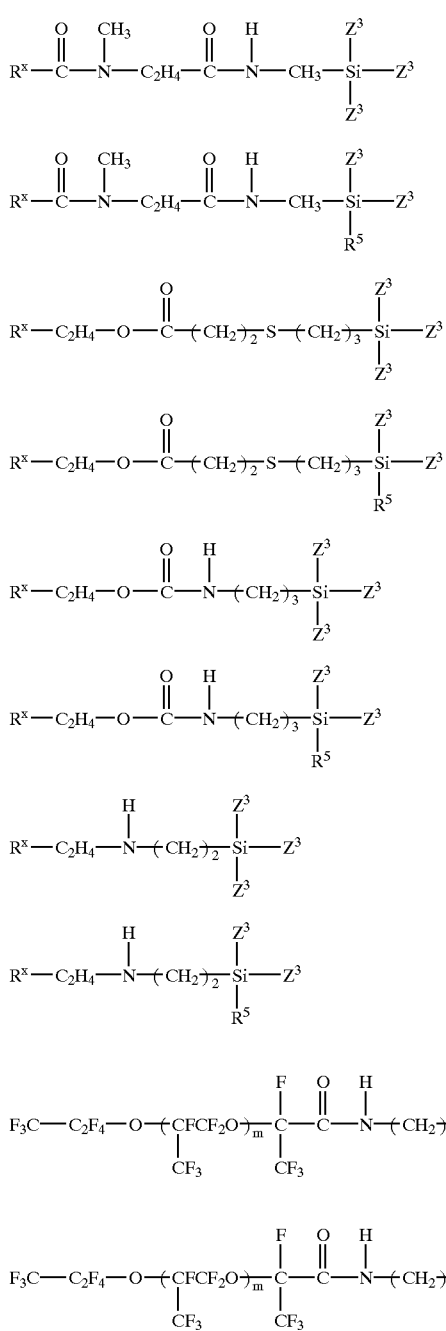

The water repellent composition of the present invention may contain a single compound (II) or two or more compounds (II).

The no fluorine-containing reactive silane compound (III) is a reactive silane compound having no fluorine atoms.

The compound (III) has a structure wherein reactive groups are directly bonded to silicon atoms. The number, per silicon atom, of the reactive groups directly bonded to silicon atoms, should better be large. The compound (III) is preferably a compound represented by $SiQ_4$ (wherein Q is an isocyanate group or a hydrolyzable group, and four Q's may be the same or different). Specifically, tetrachlorosilane, tetraisocyanate silane or a tetraalkoxysilane is preferred.

By the reactivity of such reactive groups, the compound (III) is firmly bonded to the second layer and the substrate and thus contributes to an improvement in durability.

The compound (III) may be used as it is or in the form of a hydrolysate obtained by hydrolysis. The hydrolysate of the compound (III) is a compound having e.g. silanol groups formed by hydrolysis of some or all of the reactive groups of the compound (III) in water, an acidic aqueous solution or an alkaline aqueous solution, or a compound having two or more molecules condensed by a reaction of such silanol groups. The acidic aqueous solution may, for example, be an aqueous solution of e.g. hydrochloric acid, acetic acid, sulfuric acid, phosphoric acid, sulfonic acid or methanesulfonic acid.

The water repellent composition of the present invention may contain a single compound (III) or two or more compounds (III).

When the water repellent composition of the present invention contains the compound (II) and/or the compound (III), the content is preferably from 1 to 50 parts by mass, particularly preferably from 1 to 20 parts by mass, per 100 parts by mass of the fluorine-containing organic silicon compound. Further, when the water-repellent composition employs the compound (II) and the compound (III) in combination, the content ratio of the compound (II)/the compound (III) is preferably from 9/1 to 4/6.

The water repellent composition of the present invention preferably contains, in addition to the fluorine-containing organic silicon compound, and the compound (II) or the compound (III), an acid (B) and an organic solvent (C) as other components.

The acid (B) is not particularly limited and may be suitably selected depending upon the particular purpose.

The acid (B) may, for example, be an inorganic acid such as sulfuric acid, hydrochloric acid, nitric acid or phosphoric acid, or an organic acid such as acetic acid, formic acid, p-toluenesulfonic acid or methanesulfonic acid. The acid (B) may be added as it is, to the composition, or may be formed into an aqueous solution and then added, as the case requires depending upon a particular purpose, such as acceleration of the reaction. The acid (B) or its aqueous solution may be added at any time.

The content of the acid (B) in the water repellent composition is preferably from 0.01 to 10 parts by mass per 100 parts by mass of the compound (I). When the content is at least 0.01 part by weight, an adequate effect of the addition is obtainable, and when the content is at most 10 parts by mass, the stability of the liquid will be excellent.

The acid (B) contributes to the acceleration of the reaction, which will be described hereinafter, and to the improvement of the adhesion of the surface-treated substrate with the first layer and the second layer.

The water repellent composition may be employed as it is. However, taking into consideration the operation efficiency and the thickness of the film to be formed, it is preferably used as diluted with an organic solvent (C), as the case requires.

The organic solvent (C) is not particularly limited. For example, an alcohol, a ketone, an aromatic hydrocarbon, or a paraffin type hydrocarbon is preferred. Particularly preferred is a lower alcohol such as ethyl alcohol or isopropyl alcohol, or a paraffin type hydrocarbon. The organic solvent (C) is not restricted to one type, and two or more types different in e.g. the polarity or evaporation speed, may be used as mixed.

The content of the organic solvent (C) in the water repellent composition is preferably at most 100,000 parts by mass, particularly preferably at most 10,000 parts by mass, per 100 parts by mass of the fluorine-containing organic silicon compound. When the content is at most 100,000 parts by mass, a uniform coating film can readily be formed, and the waterdrop removal property can be obtained constantly.

The water repellent composition may contain, in addition to the above components, additives, such as various metal oxides, various resins, dyes, pigments, ultraviolet absorbers or antioxidants, within a range not to impair the purpose of the present invention.

The surface-treated substrate of the present invention is a substrate having at least one surface-treated layer. It is a surface-treated substrate wherein the outermost layer in said surface-treated layer is a layer formed by the water repellent composition of the present invention. In a case of a substrate having at least two surface-treated layers, it is preferably a surface-treated substrate wherein the first layer as the outermost layer among the surface-treated layers, is a layer formed by the water repellent composition of the present invention, and the second layer in contact with the inside of the first layer is a layer formed by the composition (II) containing the fluorine-containing silane reactive compound (II) or the composition (III) containing the no fluorine-containing reactive silane compound (III). Here, the layer formed by the composition (II) has a surface having an angle of contact with water of at least 100°.

Further, in the case of a substrate having at least three surface-treated layers, it is preferably a surface-treated substrate wherein the first layer as the outermost layer among the surface-treated layers, is a layer formed by the water repellent composition of the present invention, the second layer in contact with the inside of the first layer, is a layer formed by the composition (II) containing the fluorine-containing reactive silane compound (II) and having a surface, of which an angle of contact with water is at least 100°, and the third layer in contact with the inside of the second layer, is a layer formed by the composition (III) containing the no fluorine-containing reactive silane compound (III).

By treating the substrate with the water repellent composition of the present invention, the fluorine-containing organic silicon compound as the main component of the water repellent composition, will chemically and/or physically bond to the surface of the substrate or of the second layer in contact with the inside of the outermost layer. The fluorine-containing organic silicon compound is a compound having at least one hydrolyzable group in its molecule and is considered to bond to the surface of the substrate or the second layer mainly by a chemical reaction. Further, when the water repellent composition contains the fluorine-containing reactive silane compound (II) and/or the no fluorine-containing reactive silane compound (III), a layer excellent in durability can be formed.

No special pretreatment is required prior to applying the water repellent composition to the surface of the substrate or of the second layer. Preferably, after forming the second layer as described hereinafter, the first layer as the outermost layer is formed immediately. The first layer may be formed by coating the water repellent composition on the surface by a conventional method such as brush coating, casting, rotation coating, dip coating, squeegee coating, spray coating or manual coating, followed by drying in air or in a nitrogen stream. Depending upon the treating method, an excess component may form and impair the quality of the appearance. In such a case, the appearance may be adjusted by removing the excess component by wiping with e.g. a solvent or by wiping with a dry cloth. The thickness of the first layer formed by this surface treatment is not particularly limited. However, from the viewpoint of the economical efficiency, it is preferably at most 100 nm. The lower limit is the thickness of the monomolecular layer.

In the surface-treated substrate of the present invention, the second layer is a layer obtained by treatment with the composition (II) containing the fluorine-containing reactive silane compound (II) or with the composition (III) containing the no fluorine-containing reactive silane compound (III).

The layer obtained by treatment with the composition (II) is believed to develop the excellent properties such as the waterdrop removal property, abrasion resistance, chemical resistance and weather resistance, by the reactivity of the reactive groups of the compound (II). Further, as described hereinafter, these properties can further be improved by selecting the organic groups.

The composition (II) may contain, in addition to the fluorine-containing reactive silane compound (II), other compounds or additives, depending upon the particular purpose. The additives, etc., may be selected taking into the reactivity and compatibility with the respective components. For example, no fluorine-containing water repellent materials such as both terminal reactive polydimethylsiloxane; superfine particles of various metal oxides such as silica, alumina, zirconia and titania; and various resins, may preferably be mentioned. Further, if coloration is required, a dye, a pigment or the like may be employed. The amount of additives, etc., is preferably from 0.01 to 20 parts by mass, per 100 parts by mass of the compound (II). If they are added excessively, the waterdrop removal property, the abrasion resistance, etc., tend to deteriorate, such being undesirable.

The composition (II) may be used as it is, or taking into consideration the operation efficiency, the desired thickness of the second layer, etc., it may be diluted with an organic solvent, as the case requires.

The organic solvent to be used for the composition (II) may, for example, be an acetic acid ester, an aromatic hydrocarbon, a halogenated hydrocarbon, a ketone, an ether or an alcohol. However, in a case where the compound (II) has a group having a very high reactivity, such as an isocyanate group or a chlorine atom, a solvent having an active hydrogen atom (such as a hydroxyl group) is not desirable. The organic solvent may not be restricted to one type, and a solvent mixture of two or more types different in the polarity, the evaporation speed, etc., may be used.

The content of the organic solvent in the composition (II) is preferably at most 100,000 parts by mass, per 100 parts by mass of the compound (II). When the content is at most 100,000 parts by mass, a uniform coating film can easily be formed. The content of the organic solvent can be suitably determined taking into consideration the film forming property, the operation efficiency, the stability, the film thickness, the economical efficiency, etc.

By treating with the composition (II), the compound (II) contained in the composition (II) will be chemically and/or physically bonded to the surface of the substrate or to the surface of the third layer which is an underlayer in contact with the second layer. The compound (II) is a compound having at least one isocyanate group or hydrolyzable group, as a reactive group, in its molecule, and the compound (II) is believed to be bonded to the surface of the substrate or to the surface of the third layer mainly by a chemical reaction.

No special pretreatment is required prior to applying the composition (II) to the surface of the substrate or to the surface of the third layer. Formation of the second layer by the treatment with the composition (II) can be carried out by coating the composition (II) on the surface by a known method such as brush coating, casting, rotation coating, dip coating, squeegee coating, spray coating or manual coating, following by drying in air or in a nitrogen stream. The thickness of the second layer formed by this surface treatment, is not particularly limited. However, from the viewpoint of the economical efficiency, it is preferably at most 50 nm. The lower limit is the thickness of a monomolecular layer.

In the surface-treated substrate of the present invention, the layer obtained by the treatment with the composition (III) is firmly bonded to the substrate mainly by the reactivity of the reactive groups of the compound (III) and thereby contributes to the improvement of the durability. The composition (III) may contain a single compound (III) or may contain two or more different compounds (III).

The composition (III) may contain, in addition to the compound (III) other compounds or additives depending upon the particular purpose. The additives, etc. may be selected taking into consideration the reactivity and compatibility with the respective components, and those similar to ones used in the composition (II) may be used in similar amounts.

The composition (III) may be used as it is, but is preferably used as diluted by an organic solvent. The organic solvent may be a solvent similar to one used in the composition (II).

By treating with the composition (III), the compound (III) contained in the composition (III) is chemically and/or physically bonded to the surface of the substrate. The compound (III) serves to remarkably improve the durability of the first and second layers and at the same time to improve the adhesion to the substrate.

No special pretreatment is required prior to applying the composition (III) to the surface of the substrate. However, depending upon the particular purpose, pretreatment may be carried out. For example, acid treatment with diluted hydrofluoric acid, sulfuric acid, hydrochloric acid or the like, alkali treatment with an aqueous sodium hydroxide solution or the like, or discharge treatment with plasma irradiation, corona irradiation or electron irradiation, may be carried out. Formation of the third layer by treatment with the composition (III) can be carried out by coating the composition (III) on the surface by a known method such as brush coating, casting, rotation coating, dip coating, squeegee coating, spray coating or manual coating, followed by drying in air or in a nitrogen stream. The drying can sufficiently be carried out at room temperature. However, when heat drying is carried out, the temperature and the time may be set taking into consideration the heat resistance of the substrate. The thickness of the third layer formed by this surface treatment is not particularly limited. However, in a case where the substrate is soda lime glass or the like, it may be at least 100 nm for the purpose of preventing elution of sodium ions. The thickness is preferably at most 500 nm, whereby a scratch mark will not be so distinctive. Further, it may be extremely thin, and the lower limit is the thickness of a monomolecular layer.

The surface-treated substrate of the present invention has at least the first layer as the outermost layer, but preferably has the second layer in contact with the inside of the first layer and the third layer in contact with the inside of the second layer. It is particularly preferred that the third layer is a layer obtained by the treatment with the composition (III) containing the no fluorine-containing reactive silane compound (III).

The compound (III) is firmly bonded to the second layer and the substrate mainly by the reactivity of reactive groups in the molecule and thus contributes to the improvement of the durability.

Further, a metal oxide other than silica, or its precursor compound, may be added to the compound (III), so that a mixed oxide layer or a composite oxide layer may be obtained as the third layer.

The composition (III) may contain a single compound (III) or may contain at least two compounds (III).

In the surface-treated substrate of the present invention, the thicknesses of the respective layers to be formed, can suitably be controlled by the concentrations of the compositions, the coating conditions, the heating conditions, etc. The thicknesses of the respective layers are as described above, respectively. However, the thickness of the entire surface-treated layer is preferably at most 1,000 nm taking into consideration also the economical effect.

In the present invention, the substrate is not particularly limited. For example, an inorganic material such as metal, plastic, glass or ceramics, an organic material, or a combination thereof (such as a composite material or a laminated material) is preferably mentioned. Further, the substrate may have a layer such as a vapor deposited film, a sputtered film or various films obtained by e.g. a wet method, on the surface of e.g. metal. For example, one having a coated surface such as a coated metal plate or one having a surface-treated layer such as a surface-treated glass, may be preferably mentioned. Particularly preferred among them is a substrate made of a transparent material such as glass or plastic, since the effects of the present invention are particularly remarkable.

The shape of the substrate on which a surface-treated layer is formed, is not limited to a flat plate and may be an optional shape depending upon the particular purpose, such as one having a curvature partly or entirely.

The process for producing the surface-treated substrate of the present invention is not particularly limited. However, as a preferred process, a process may be mentioned which comprises a step of treating the surface of a substrate with the composition (II) or the composition (III) to form a second layer and a step of treating the surface of the second layer with the water repellent composition to form the first layer.

The step of treating with the composition (II) or the composition (III) to form the second layer, or the method of treating the surface of the second layer with the water repellent composition to form the first layer, is preferably carried out by the method already described.

Further, it is preferred to have a drying step after forming the first layer. The drying step may be carried out at room temperature or by heating at a temperature of from 80 to 300° C. for from 1 to 60 minutes. Room temperature drying or heat drying is selected depending upon the particular purpose, etc. Room temperature drying is economically advantageous, since no special installation will be required. Especially when the object to be treated is incorporated in a separate article (such as a glass incorporated in an automobile), it is difficult to carry out heat drying, and room temperature drying will be selected. On the other hand, heat drying has a merit that the drying speed is high, or it brings about a product excellent in the durability.

In a case where the surface-treated substrate of the present invention has a third layer inside of the second layer, it is preferred to employ a process which comprises a step of treating the surface of a substrate with the composition (III) to form the third layer, a step of treating the surface of the third layer with the composition (II) to form the second layer, and a step of treating the surface of the second layer with the water repellent composition to form the first layer. The methods for forming the respective layers are preferably carried out by the above-mentioned methods.

Further, a heating step may be provided after forming the third layer and prior to forming the second layer. In such a case, it is preferred to carry out heating at a temperature of at least 400° C., preferably from 500 to 700° C. for from 1 to 60 minutes. There is a merit such that by the heating, the adhesion of the third layer with the substrate and the density of the third layer will be improved, and the durability will be improved.

The surface-treated substrate of the present invention preferably has three surface-treated layers. The first layer obtained by the treatment with the water repellent composition contributes to the development of the excellent waterdrop falling property. The second layer obtained by the treatment with the composition (II), contributes to the development of the excellent durability of water repellency. The third layer obtained by the treatment with the composition (III), serves to firmly bond the substrate with the second layer.

The present invention provides effects which exceed the effects expected when materials having different functions are laminated. Namely, the first layer obtained by the treatment with the water repellent composition is a coating film containing the fluorine-containing organic silicon compound as the main component, and the second layer obtained by the treatment with the composition (II) is a fluorine-containing silicon coating film. According to the conventional knowledge, it is very difficult to form a silicon coating film having a high surface energy on the surface of a fluorine-containing silicon coating film having a low surface energy.

However, by the construction of the materials of the present invention, such formation is possible. The details of this mechanism are not known, but it is considered that in the combination of the compositions selected by the present invention, a strong intermolecular mutual action which has not been expected heretofore, will work between the material forming the first layer and the material forming the second layer. A part of such a mutual action is considered to be a mixing (mutual diffusion) between the material for forming the first layer and the material for forming the second layer. The angle of contact with water of the surface of the outermost layer in a case where the water repellent composition is applied to the surface of the second layer as in the present invention, is large as compared with e.g. a case where the water repellent composition is directly applied to the surface of glass. This is considered attributable to the fact that the fluorine-containing reactive silane compound (II) as the material for forming the second layer having a large angle of contact, has diffused in the outermost layer during the formation of the outermost layer, and a part thereof is exposed on the surface of the outermost layer.

Further, the outermost layer alone does not show so high durability of water repellency, but when formed on the surface of the second layer, it presents excellent durability. Therefore, it is considered that there is an synergistic effect which has not heretofore been expected, between the outermost layer and the second layer.

Namely, the concept of layers in the present invention is such that the respective layers can be distinguished macroscopically, but microscopically, their boundary lines are not clear, and the respectively adjacent layers are mutually mixed partly or wholly at the interface. The present invention has such a layered structure, whereby the waterdrop falling property and the durability of water repellency of the outermost layer will be excellent due to not only the waterdrop falling property derived from the water repellent composition but also the durability of water repellency derived from the fluorine-containing reactive silane compound (II) forming the second layer.

The applications of the surface-treated substrate of the present invention are not particularly limited, but it is particularly useful for equipments for transports. The equipments for transports are meant for window glasses (such as front glasses, side glasses or rear glasses), mirrors, surface panels of display instruments, surface panels of measuring instruments and other constituting components (such as bodies or bumpers) for transports such as electric rail cars, buses, trucks, automobiles, ships and aircrafts.

An equipment for transports may be composed solely of the surface-treated substrate of the present invention or one in which the surface-treated substrate is incorporated. For example, the former may be a window glass for an automobile, and the latter may be a back mirror component for an automobile, in which the mirror is incorporated.

With the surface-treated substrate or the equipment for transports, waterdrops deposited on the surface are repelled by the waterdrop removal property. Especially when the transport is moving, waterdrops will move on the surface quickly by the wind pressure and will not stay as waterdrops, whereby various adverse effects induced by water can be avoided.

Especially in an application at a see-through portion such as a window glass, it will be easy to secure visibility by dissipation of waterdrops. Namely, the surface-treated substrate or the equipment for transports, of the present invention, is excellent not only in the waterdrop falling property but also in the water repellency. Accordingly, when raindrops or the like are deposited on the surface, they will flow down as waterdrops. On the other hand, on a conventional surface which is poor in water repellency, water flows down in a film state, whereby it is difficult to secure visibility.

Further, the surface-treated substrate of the present invention is excellent not only in the initial waterdrop falling property and the water repellency but also in the abrasion resistance, weather resistance and boiling resistance, by the combination of the outermost layer, the second layer and the third layer. Further, it is also excellent in chemical resistance, whereby it can be used along the seashore or at a region where the substrate will be in direct contact with sea water.

When the surface-treated substrate of the present invention has the third layer, it will be excellent particularly in durability. For example, when it is used for a front glass of an automobile, the outermost layer and the second layer can maintain their properties for from 3 to 5 years without peeling or falling.

When the surface-treated substrate of the present invention has no third layer, there is a merit such that at the time of repair, the outermost layer and the second layer may be peeled, and new outermost layer and second layer can easily be formed.

Further, the surface-treated substrate or the equipment for transports, of the present invention, is excellent in water repellency, whereby even in an environment of e.g. below the freezing point, waterdrops will not freeze on the surface, or even when they will be frozen slightly, thawing is very fast. Further, there is no substantial deposition of waterdrops, whereby the number of cleaning operations can be reduced, and such cleaning is easy. This is very advantageous also from the viewpoint of keeping good appearance.

Now, the present invention will be described in further detail with reference to Examples. Example 1 is a Preparation Example, Examples 2 to 22 are Working Examples of the present invention and Examples 23 to 25 are Comparative Examples. In these Examples, various physical properties were measured by the following methods, and the results are shown in Table 1 (unit: degree).

1. Water Drop Removal Property 1-a) The contact angle of a waterdrop having a diameter of 1 mm, placed on the surface of a sample, was measured. Measurements were carried out at five different locations on the surface, and the average value was indicated.

1-b) A waterdrop of 50 µl was dropped on the surface of a sample which was horizontally held, and then the sample was gradually inclined, whereby the angle (the falling angle) of the sample from the horizontal plane when the waterdrop started to fall, was measured. The smaller the falling angle, the better the waterdrop removal property.

2. Abrasion Resistance

A sample was subjected to an abrasion test under the following test conditions, whereupon the contact angle and the falling angle were measured.

Test machine: Reciprocal type traverse testing machine, manufactured by KNT Co.

Test conditions: Flannel cloth, load: 1 kg, number of abrasion: 3,000 reciprocations 3. Weather Resistance A weather resistance test was carried out for 200 cycles, each cycle consisted of irradiation of ultraviolet rays for 8 hours (70° C.), followed by exposure to wetting for 4 hours (50° C.), and then the contact angle and the falling angle were measured.

4. Boiling Resistance

A sample was immersed in boiling water for 3 hours, and then, the contact angle and the falling angle were measured.

5. Sample Substrate

Preliminarily cleaned glass plate of 10 cm×10 cm and having a thickness of 3 mm.

6. Preparation of a Sample

To a sample substrate, 0.5 ml of a treating agent was dropped in an environment of a temperature of 25° C. and a humidity of 50%, then spread in the same manner as waxing an automobile, and left to stand in the same environment for one day to obtain a sample.

EXAMPLE 1

Into a 100 ml three necked flask equipped with a stirrer, 13.8 g of hexamethylcyclotrisiloxane, 10 g of heptadecafluorooctylethyldimethylsilanol and 60 ml of tetrahydrofuran were charged, and the internal temperature was adjusted to 20° C.

Then, 20 ml of a n-hexane solution of n-butyl lithium (15 mass %) was added thereto, and the reaction was carried out for 3 hours. Further, 10 g of trimethoxychlorosilane was added thereto, followed by stirring for 1 hour.

After removing lithium chloride by filtration, from the filtrate, volatile components such as tetrahydrofuran and excess trimethoxychlorosilane were distilled off by means of a rotary evaporator (manufactured by Toyo Rika Kikai K.K.) at 5 mmHg at 100° C., to obtain 21.5 g of a colorless transparent liquid. The obtained liquid was confirmed to be $F(CF_2)_8CH_2CH_2$—$Si(CH_3)_2$—$(OSi(CH_3)_2)_9$—OSi—$(OCH_3)_3$. The results of measurements of $^1$H-NMR spectrum, $^{29}$Si-NMR spectrum and IR of the obtained liquid, are shown below.

[$^1$H-NMR (solvent: CDCl$_3$ (heavy chloroform), unit: ppm)] Si—OC$\underline{H}_3$; 3.6, $F(CF_2)_8C\underline{H}_2CH_2$—Si; 2.1, $F(CF_2C\underline{H}_2$—Si; 0.8, Si—C$\underline{H}_3$; 0–0.2.

[$^{29}$Si—NMR (Solvent: CDCl$_3$ (heavy chloroform), unit: ppm)] $F(CF_2)_8CH_2CH_2$—$\underline{Si}(CH_3)_2$—; 7, $F(CF_2)_8CH_2$—$\underline{Si}(CH_3)_2$—$O\underline{Si}(CH_3)_2$; —21, $OSi(CH_3)_2$—(O$\underline{Si}(CH_3)_2)_7$—$OSi(CH_3)_2$; — 22, —O $\underline{Si}(CH_3)_2$—$Osi(OCH_3)_3$; —20, —$OSi(CH_3)_2$—O $\underline{Si}(OCH_3)_3$; —85.

[IR (unit: cm$^{-1}$)] —CH$_3$: 2964, —CF$_2$—: 1262, Si—O—Si: 1025, 1097, Si—CH$_3$: 803, C—F$_3$: 704.

EXAMPLE 2

Into a glass container equipped with a stirrer and a thermometer, 5.0 g of a compound (a-1) of the following formula (a-1) and 95.0 g of isopropyl alcohol were put and stirred at 25° C. for 10 minutes to obtain a treating liquid 1A. Further, into a separate glass container equipped with a stirrer and a thermometer, 10 g of p-toluenesulfonic acid and 90 g of isopropyl alcohol were put and stirred at 25° C. for 10 minutes to obtain a treating liquid 1B.

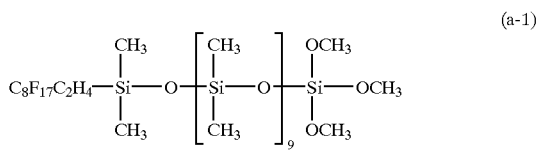
(a-1)

A sample was prepared by using a treating agent immediate after obtained by mixing 50 g of the treating liquid 1A and 3 g of the treating liquid 1B. Using this sample, the above-mentioned measurements were carried out.

EXAMPLES 3 to 5

A sample was prepared in the same manner as in Example 2 except that instead of the compound (a-1) in Example 2, a compound of the following formula (a-2), (a-3) or (a-4) was used. Using this sample, the above-mentioned measurements were carried out.

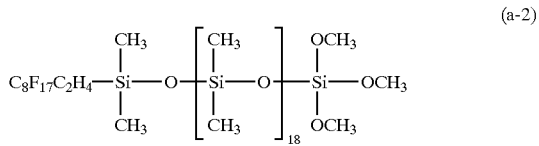
(a-2)

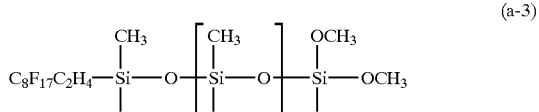
(a-3)

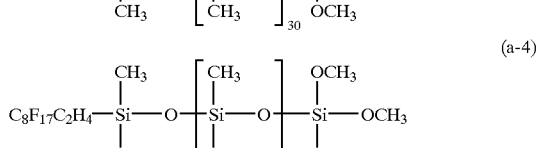
(a-4)

EXAMPLE 6

Into a glass container equipped with a stirrer and a thermometer, 5.0 g of a compound (a-5) of the following formula (a-5), and 95.0 g of ethyl acetate were put and stirred at 25° C. for 10 minutes, to obtain a treating agent. Using the obtained treating agent, a sample was prepared. Using this sample, the above-mentioned measurements were carried out.

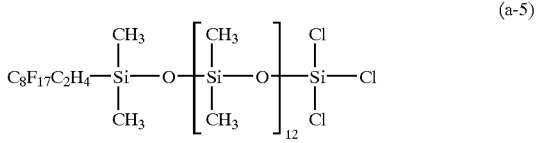

(a-5)

EXAMPLE 7

A sample was prepared in the same manner as in Example 6 except that instead of the compound (a-5) in Example 6, a compound of the following formula (a-6) was used. Using this sample, the above-mentioned measurements were carried out.

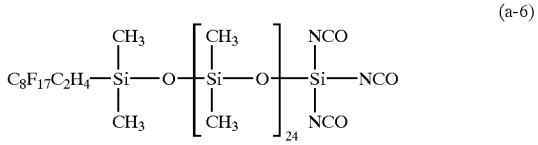

(a-6)

EXAMPLE 8

Into a glass container equipped with a stirrer and a thermometer, 5.0 g of the compound (a-1), 90.0 g of ethyl acetate and 5.0 g of an aqueous nitric acid solution (1 mass %) were put, stirred at 25° C. for 3 hours and then left to stand for 3 days to obtain a treating agent. Using the obtained treating agent, a sample was prepared. Using this sample, the above-mentioned measurements were carried out.

EXAMPLE 9

Into a glass container equipped with a stirrer and a thermometer, 3.0 g of $F(CF_2)_8C_2H_4SiCl_3$ and 97.0 g of ethyl acetate were put, and stirred at 25° C. for 10 minutes to obtain a treating agent 9.

Into a separate glass container equipped with a stirrer and a thermometer, 5.0 g of the compound (a-1) and 95.0 g of isopropyl alcohol were put and stirred at 25° C. for 10 minutes to obtain a treating liquid 9A.

Further, into a separate glass container equipped with a stirrer and a thermometer, 10 g of p-toluenesulfonic acid and 90 g of isopropyl alcohol were put and stirred at 25° C. for 10 minutes to obtain a treating liquid 9B.

In an environment at a temperature of 27° C. under a humidity of 60%, 0.5 ml of the treating agent 9 was dropped on a sample substrate and spread in the same manner as waxing an automobile. Further, under the same environment, it was left to stand for 1 minute, then 0.5 ml of a treating agent 9' immediately after obtained by mixing 50 g of the treating liquid 9A and 3 g of the treating liquid 9B, was dropped and spread in the same manner as waxing an automobile. This was left to stand for 1 day in an environment at a temperature of 25° C. under a humidity of 50%, to obtain a sample. Using this sample, the above-mentioned measurements were carried out.

EXAMPLE 10

Into a glass container equipped with a stirrer and a thermometer, 4.0 g of $F(CF_2)_8C_2H_4Si(OCH_3)_3$, 92.0 g of isopropyl alcohol and 4.0 g of an aqueous nitric acid solution (1 mass %) were put, stirred at 25° C. for 3 hours and then left to stand for 3 days to obtain a treating agent 10. A sample was prepared in the same manner as in Example 9 except that instead of the treating agent 9 in Example 9, the treating agent 10 was employed. Using this sample, the above-mentioned measurements were carried out.

EXAMPLE 11

Into a glass container equipped with a stirrer and a thermometer, 3.0 g of $Si(NCO)_4$ and 97.0 g of N-butyl acetate were put and stirred at 25° C. for 10 minutes to obtain a treating agent 11.

A sample was prepared in the same manner as in Example 9 except that instead of the treating agent 9 in Example 9, a treating agent 11 was employed. Using this sample, the above-mentioned measurements were carried out.

EXAMPLE 12

Into a glass container equipped with a stirrer and a thermometer, 3.0 g of $Si(OCH_3)4$, 93.5 g of ethyl alcohol and 1.5 g of an aqueous nitric acid solution (1 mass %) were charged, stirred at 25° C. for 3 hours and then left to stand for 1 day, to obtain a treating agent 12.

A sample was prepared in the same manner as in Example 9 except that instead of the treating agent 9 in Example 9, a treating agent 12 was employed. Using this sample, the above-mentioned measurements were carried out.

EXAMPLE 13

In an environment at a temperature of 27° C. under a humidity of 60%, 0.5 ml of the treating agent 11 was dropped on the sample substrate, spread in the same manner as waxing an automobile and left to stand for 1 minute under the same environment. Then, on its surface, the treating agent 9 was coated and spread in the same manner and left to stand, whereupon on the surface, the treating agent 9' was coated and spread in the same manner and left to stand for 1 day in the same environment to obtain a sample. Using this sample, the above-mentioned measurements were carried out.

EXAMPLE 14

Into a glass container equipped with a stirrer and a thermometer, 1.0 g of a compound (a-13) of the following formula (a-13), 4.0 g of $F(CF_2)_8C_2H_4SiCl_3$ and 95.0 g of n-butyl acetate were put and stirred at 25° C. for 10 minutes to obtain a treating agent 14.

Using the obtained treating agent 14, a sample was prepared. Using this sample, the above-mentioned measurements were carried out.

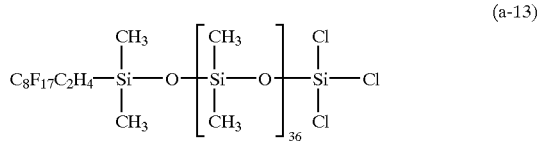

(a-13)

EXAMPLE 15

A sample was prepared in the same manner as in Example 9 except that instead of the treating agent 9' in Example 9, the treating agent 14 was used. Using this sample, the above-mentioned measurements were carried out.

EXAMPLE 16

Into a glass container equipped with a stirrer and a thermometer, 4.0 g of the compound (a-13), 1.0 g of Si(NCO)₄, and 95.0 g of n-butyl acetate were put and stirred at 25° C. for 10 minutes to obtain a treating agent 16. Using the obtained treating agent 16, a sample 16 was prepared. Using this sample, the above-mentioned measurements were carried out.

EXAMPLE 17

A sample was prepared in the same manner as in Example 9 except that instead of the treating agent 9 in Example 9, the treating agent 11 was employed, and instead of the treating agent 9', the treating agent 16 was employed. Using this sample, the above-mentioned measurements were carried out.

EXAMPLE 18

A sample was prepared in the same manner as in Example 13 except that instead of the treating agent 9' in Example 13, the treating agent 14 was employed. Using this sample, the above-mentioned measurements were carried out.

EXAMPLE 19

The sample obtained in Example 13 was further heated at 200° C. for 60 minutes to obtain a sample. Using this sample, the above-mentioned measurements were carried out.

EXAMPLE 20

A sample was prepared in the same manner as in Example 13 except that instead of coating and spreading the treating agent 11 and then leaving it to stand for 1 minute in Example 13, heating was carried out at 650° C. for 5 minutes. Using this sample, the above-mentioned measurements were carried out.

EXAMPLE 21

Into a glass container equipped with a stirrer and a thermometer, 4.0 g of the compound (a-1), 1.0 g of Si(OCH₃)₄, 90.0 g of isopropyl alcohol and 5.0 g of an aqueous nitric acid solution (1 mass %) were charged, stirred for 3 hours and left to stand for 3 days to obtain a treating agent.

Using the obtained treating agent, a sample was prepared. Using this sample, the above-mentioned measurements were carried out.

EXAMPLE 22

Into a glass container equipped with a stirrer and a thermometer, 1.0 g of the compound (a-1), 4.0 g of F(CF₂)₈C₂H₄Si(OCH₃)₃, 90.0 g of isopropyl alcohol and 5.0 g of a 1 mass % nitric acid aqueous solution, were charged, stirred for 3 hours and left to stand for 3 days to obtain a treating agent.

Using the obtained treating agent, a sample was prepared. Using this sample, the above-mentioned measurements were carried out.

EXAMPLE 23

Using the treating agent 9, a sample was prepared. Using this sample, the above-mentioned measurements were carried out.

EXAMPLE 24

Into a glass container equipped with a stirrer and a thermometer, 5.0 g of a compound of the following formula (R2) and 95.0 g of isopropyl alcohol were charged and stirred at 25° C. for 10 minutes to obtain a treating liquid R2A.

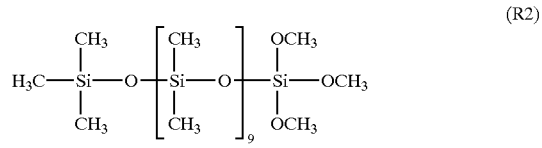

(R2)

A sample was prepared by using a treating agent immediately after obtained by mixing 50 g of the treating agent R2A and 3 g of the treating agent 9. Using this sample, the above-mentioned measurements were carried out.

EXAMPLE 25

Into a glass container equipped with a stirrer and a thermometer, 5.0 g of a compound of the following formula (R3) and 95.0 g of isopropyl alcohol were charged and stirred at 25° C. for 10 minutes to obtain a treating agent R3A.

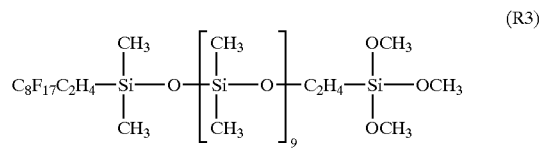

(R3)

A sample was prepared by using a treating agent obtained by mixing 50 g of the treating agent R3A and 3 g of the treating agent 9. Using this sample, the above-mentioned measurements were carried out.

TABLE 1

| Ex. | Initial stage | | Abrasion resistance | | Weather resistance | | Boiling resistance | |
| --- | --- | --- | --- | --- | --- | --- | --- | --- |
| | CA | FA | CA | FA | CA | FA | CA | FA |
| 2 | 106 | 5 | 102 | 8 | 82 | 27 | 80 | 26 |
| 3 | 107 | 3 | 104 | 4 | 88 | 20 | 82 | 20 |
| 4 | 107 | 3 | 102 | 8 | 81 | 25 | 80 | 24 |
| 5 | 104 | 8 | 102 | 10 | 90 | 18 | 90 | 18 |
| 6 | 106 | 5 | 104 | 6 | 90 | 16 | 88 | 18 |
| 7 | 106 | 5 | 104 | 6 | 90 | 18 | 88 | 19 |
| 8 | 106 | 6 | 104 | 7 | 82 | 25 | 84 | 20 |
| 9 | 110 | 5 | 108 | 8 | 98 | 13 | 98 | 13 |
| 10 | 110 | 5 | 109 | 6 | 96 | 13 | 99 | 13 |
| 11 | 106 | 2 | 105 | 5 | 95 | 13 | 95 | 13 |
| 12 | 106 | 4 | 104 | 6 | 95 | 13 | 98 | 12 |
| 13 | 110 | 5 | 108 | 8 | 102 | 12 | 104 | 12 |
| 14 | 109 | 6 | 105 | 9 | 86 | 16 | 89 | 16 |
| 15 | 109 | 4 | 106 | 6 | 98 | 14 | 98 | 14 |
| 16 | 105 | 3 | 102 | 5 | 88 | 18 | 89 | 18 |
| 17 | 106 | 5 | 102 | 8 | 96 | 17 | 95 | 17 |
| 18 | 111 | 5 | 107 | 7 | 105 | 11 | 103 | 12 |
| 19 | 110 | 6 | 108 | 8 | 105 | 10 | 107 | 8 |
| 20 | 110 | 6 | 106 | 8 | 103 | 11 | 105 | 9 |
| 21 | 106 | 5 | 103 | 7 | 86 | 20 | 85 | 21 |
| 22 | 110 | 9 | 108 | 10 | 86 | 15 | 85 | 15 |
| 23 | 110 | 22 | 106 | 26 | 102 | 35 | 106 | 42 |
| 24 | 102 | 5 | 97 | 8 | 78 | 35 | 69 | 36 |
| 25 | 105 | 5 | 102 | 15 | 66 | 41 | 80 | 32 |

CA: Contact angle
FA: Falling angle

As described in the foregoing, the fluorine-containing organic silicon compound of the present invention is a novel compound useful as a main component of a water repellent composition.

The water repellent composition of the present invention contains such a novel fluorine-containing organic silicon compound as the main component, and when coated on various substrates, it is capable of imparting a waterdrop removal property, and it is excellent in the abrasion resistance, weather resistance, boiling resistance and chemical resistance. Accordingly, it is capable of providing surface treatment whereby such properties can be maintained for a long period of time.

The surface-treated substrate of the present invention has a waterdrop removal property and is excellent in the abrasion resistance, weather resistance, boiling resistance and chemical resistance, whereby such properties will last semi-permanently.

Further, according to the process of the present invention, such a surface-treated substrate can be produced.

The equipment for transports of the present invention has a waterdrop removal property, and such a property will last for a long period of time, whereby there will be no problem due to deposition of water, such as deterioration of the performance.

The entire disclosure of Japanese Patent Application No. 2000-311829 filed on Oct. 12, 2000 including specification, claims and summary are incorporated herein by reference in its entirety.

What is claimed is:

1. A fluorine-containing organic silicon compound of the following formula (1):

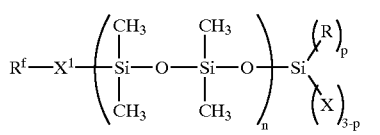

wherein $R^f$ is a fluorine-containing $C_{1-20}$ monovalent organic group, $X^1$ is an alkylene group, n is an integer of from 0 to 100, R is a $C_{1-5}$ monovalent hydrocarbon group, X is a hydrolyzable group, and p is 1 or 2.

2. A water repellent composition containing the fluorine-containing organic silicon compound as defined in claim 1.

3. The water repellent composition according to claim 2, which further contains a fluorine-containing reactive silane compound (II) and/or a no fluorine-containing reactive silane compound (III), which is capable of forming a surface having an angle of contact with water of at least 100°.

4. The water repellent composition according to claim 3, wherein the fluorine-containing reactive silane compound (II) is at least one member selected from reactive silane compounds of the following formulae (IIA) and (IIB):

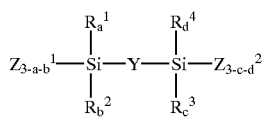

wherein each of $R^1$, $R^2$, $R^3$ and $R^4$ is a hydrogen atom or a $C_{1-21}$ monovalent organic group, Y is a bivalent organic group, provided that at least one of $R^1$, $R^2$, $R^3$, $R^4$ and Y is a fluorine-containing organic group, each of $Z^1$ and $Z^2$ is an isocyanate group or a hydrolyzable group, each of a and b is 0, 1 or 2, provided $0 \leq a+b \leq 2$, and each of c and d is 0, 1 or 2, provided $0 \leq c+d \leq 2$; and

wherein each of $R^5$, $R^6$ and $R^7$ is a hydrogen atom or a $C_{1-21}$ monovalent organic group, provided that at least one of $R^5$, $R^6$ and $R^7$ is a fluorine-containing organic group, $Z^3$ is an isocyanate group or a hydrolyzable group, and each of e, g and h is 0, 1 or 2, provided $1 \leq (e+g+h) \leq 3$.

5. The water repellent composition according to claim 3, wherein the fluorine-containing organic group is a $C_{3-21}$ polyfluoroalkyl group or a $C_{2-16}$ polyfluoroalkylene group.

6. The water repellent composition according to claim 3, wherein the no fluorine-containing silane compound (III) is at least one member selected from the group consisting of a tetraisocyanate silane, a tetraalkoxysilane and hydrolysates thereof.

7. A surface-treated substrate having at least one surface-treated layer, wherein the outermost layer of the surface-treated layer is a layer formed by the water repellent composition as defined in claim 2.

8. A surface-treated substrate having at least one surface-treated layer, wherein the outermost layer of the surface-treated layer is a layer formed by the water repellent composition as defined in claim 3.

9. A surface-treated substrate which is a substrate having at least three surface-treated layers, wherein the first layer as the outermost layer among the surface-treated layers, is a layer formed by the water repellent composition as defined in claim 2; the second layer in contact with the inside of the first layer, is a layer formed by a composition (II) containing a fluorine-containing reactive silane compound (II) and having a surface, of which an angle of contact with water is at least 100°; and the third layer in contact with the inside of the second layer, is a layer formed by a composition (III) containing a no fluorine-containing reactive silane compound (III).

10. A surface-treated substrate which is a substrate having at least three surface-treated layers, wherein the first layer as the outermost layer among the surface-treated layers, is a layer formed by the water repellent composition as defined in claim 3; the second layer in contact with the inside of the first layer, is a layer formed by a composition (II) containing a fluorine-containing reactive silane compound (II) and having a surface, of which an angle of contact with water is at least 100°; and the third layer in contact with the inside of the second layer, is a layer formed by a composition (III) containing a no fluorine-containing reactive silane compound (III).

11. A process for producing the surface-treated substrate as defined in claim 9, which comprises a step of treating the surface of a substrate with the composition (III) to form the third layer, a step of then treating the surface of the third layer with the composition (II) to form the second layer, a step of further treating the surface of the second layer with the water repellent composition as defined claim 2 to form the outermost layer, and a step of finally drying at room temperature.

12. A process for producing the surface-treated substrate as defined in claim 10, which comprises a step of treating the surface of a substrate with the composition (III) to form the third layer, a step of then treating the surface of the third layer with the composition (II) to form the second layer, a step of further treating the surface of the second layer with the water repellent composition as defined in claim 3 to form the outermost layer, and a step of finally drying at room temperature.

13. An equipment for transports, which comprises the surface-treated substrate as defined in claim 7.

14. An equipment for transports, which comprises the surface-treated substrate as defined in claim 8.

15. A water repellent composition comprising a fluorine-containing organic silicon compound of the following formula (1):

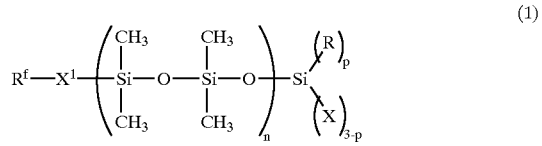

(1)

wherein $R^f$ is a fluorine-containing $C_{1-20}$ monovalent organic group, $X^1$ is an alkylene group, n is an integer of from 0 to 100, R is a $C_{1-5}$ monovalent hydrocarbon group, X is a hydrolyzable group, and p is 0, 1 or 2, further containing a fluorine-containing reactive silane compound (II) and/or a no fluorine-containing reactive silane compound (III), which is capable of forming a surface having an angle of contact with water of at least 100°.

16. The water repellent composition according to claim 15, wherein the fluorine-containing reactive silane compound (II) is at least one member selected from reactive silane compounds of the following formulae (IIA) and (IIB):

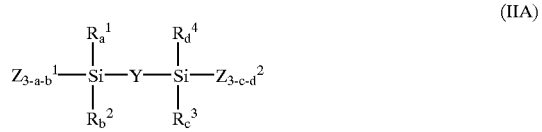

(IIA)

wherein each of $R^1$, $R^2$, $R^3$ and $R^4$ is a hydrogen atom or a $C_{1-21}$ monovalent organic group, Y is a bivalent organic group, provided that at least one of $R^1$, $R^2$, $R^3$, $R^4$ and Y is a fluorine-containing organic group, each of $Z^1$ and $Z^2$ is an isocyanate group or a hydrolyzable group, each of a and b is 0, 1 or 2, provided $0 \leq a+b \leq 2$, and each of c and d is 0, 1 or 2, provided $0 \leq c+d \leq 2$ and

(IIB)

wherein each of $R^5$, $R^6$ and $R^7$ is a hydrogen atom or a $C_{1-21}$ monovalent organic group, provided that at least one of $R^5$, $R^6$ and $R^7$ is a fluorine-containing organic group, $Z^3$ is an isocyanate group or a hydrolyzable group, and each of e, g and h is 0, 1 or 2, provided $1 \leq (e+g+h) \leq 3$.

17. The water repellent composition according to claim 15, wherein the fluorine-containing organic group is a $C_{3-21}$ polyfluoroalkyl group or a $C_{2-16}$ polyfluoroalkylene group.

18. The water repellent composition according to claim 15, wherein the no fluorine-containing silane compound (III) is at least one member selected from the group consisting of a tetraisocyanate silane, a tetraalkoxysilane and hydrolysates thereof.

19. A surface-treated substrate having at least one surface-treated layer, wherein the outermost layer of the surface-treated layer is a layer formed by the water repellent composition as defined in claim 15.

20. A surface-treated substrate which is a substrate having at least three surface-treated layers, wherein the first layer as the outermost layer among the surface-treated layers, is a layer formed by a water repellent composition comprising a fluorine-containing organic silicon compound of the following formula (1):

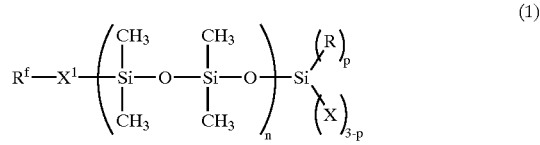

(1)

wherein $R^f$ is a fluorine-containing $C_{1-20}$ monovalent organic group, $X^1$ is an alkylene group, n is an integer of from 0 to 100, R is a $C_{1-5}$ monovalent hydrocarbon group, X is a hydrolyzable group, and p is 0, 1 or 2, the second layer in contact with the inside of the first layer, is a layer formed by a composition (II) containing a fluorine-containing reactive silane compound (II) and having a surface, of which an angle of contact with water is at least 100°; and the third layer in contact with the inside of the second layer, is a layer formed by a composition (III) containing a no fluorine-containing reactive silane compound (III).

21. A surface-treated substrate which is a substrate having at least three surface-treated layers, wherein the first layer as the outermost layer among the surface-treated layers, is a layer formed by the water repellent composition as defined in claim 15; the second layer in contact with the inside of the first layer, is a layer formed by a composition (II) containing a fluorine-containing reactive silane compound (II) and having a surface, of which an angle of contact with water is at least 100°; and the third layer in contact with the inside of the second layer, is a layer formed by a composition (III) containing a no fluorine-containing reactive silane compound (III).

22. A process for producing the surface-treated substrate as defined in claim 20, which comprises a step of treating the surface of a substrate with the composition (III) to form the third layer, a step of then treating the surface of the third layer with the composition (II) to form the second layer, a step of further treating the surface of the second layer with the water repellent composition as defined claim 2 to form the outermost layer, and a step of finally drying at room temperature.

23. A process for producing the surface-treated substrate as defined in claim 21, which comprises a step of treating the surface of a substrate with the composition (III) to form the third layer, a step of then treating the surface of the third layer with the composition (II) to form the second layer, a step of further treating the surface of the second layer with the water repellent composition as defined in claim 3 to form the outermost layer, and a step of finally drying at room temperature.

24. An equipment for transports, which comprises the surface-treated substrate as defined in claim 19.

25. A fluorine-containing organic silicon compound of the following formula

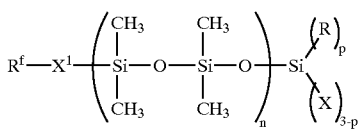

(1)

wherein $R^f$ is a fluorine-containing $C_{1-20}$ monovalent organic group, $X^1$ is an alkylene group, n is an integer of from 0 to 100, R is a $C_{1-5}$ monovalent hydrocarbon group, X is a chlorine atom, NCO or an acyloxy group, and p is 0, 1 or 2.

26. A water-repellent composition containing the fluorine-containing organic silicon compound as defined in claim 25.

27. The water repellent composition according to claim 26, which further contains a fluorine-containing reactive silane compound (II) and/or a no fluorine-containing reactive silane compound (III), which is capable of forming a surface having an angle of contact with water of at least 100°.

28. The water repellent composition according to claim 27, wherein the fluorine-containing reactive silane compound (II) is at least one member selected from reactive silane compounds of the following formulae (IIA) and (IIB):

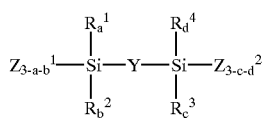

(IIA)

wherein each of $R^1$, $R^2$, $R^3$ and $R^4$ is a hydrogen atom or a $C_{1-21}$ monovalent organic group, Y is a bivalent organic group, provided that at least one of $R^1$, $R^2$, $R^3$, $R^4$ and Y is a fluorine-containing organic group, each of $Z^1$ and $Z^2$ is an isocyanate group or a hydrolyzable group, each of a and b is 0, 1 or 2, provided $0 \leq a+b \leq 2$, and each of c and d is 0, 1 or 2, provided $0 \leq c+d \leq 2$; and

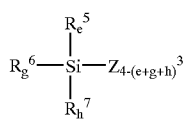

(IIB)

wherein each of $R^5$, $R^6$ and $R^7$ is a hydrogen atom or a $C_{1-21}$ monovalent organic group, provided that at least one of $R^5$, $R^6$ and $R^7$ is a fluorine-containing organic group, $Z^3$ is an isocyanate group or a hydrolyzable group, and each of e, g and h is 0, 1 or 2, provided $1 \leq (e+g+h) \leq 3$.

29. The water repellent composition according to claim 26, wherein the fluorine-containing organic group is a $C_{3-21}$ polyfluoroalkyl group or a $C_{2-16}$ polyfluoroalkylene group.

30. The water repellent composition according to claim 26, wherein the no fluorine-containing silane compound (III) is at least one member selected from the group consisting of a tetraisocyanate silane, a tetraalkoxysilane and hydrolysates thereof.

31. A surface-treated substrate having at least one surface-treated layer, wherein the outermost layer of the surface-treated layer is a layer formed by the water repellent composition as defined in claim 26.

32. A surface-treated substrate which is a substrate having at least one surface-treated layer, wherein the outermost layer of the surface-treated layer is a layer formed by the water repellent composition as defined in claim 26.

33. A surface-treated substrate which is a substrate having at least three surface-treated layers, wherein the first layer as the outermost layer among the surface-treated layers, is a layer formed by the water repellent composition as defined in claim 25; the second layer in contact with the inside of the first layer, is a layer formed by a composition (II) containing a fluorine-containing reactive silane compound (II) and having a surface, of which an angle of contact with water is at least 100°; and the third layer in contact with the inside of the second layer, is a layer formed by a composition (III) containing a no fluorine-containing reactive silane compound (III).

34. A surface-treated substrate which is a substrate having at least three surface-treated layers, wherein the first layer as the outermost layer among the surface-treated layers, is a layer formed by the water repellent composition as defined in claim 26; the second layer in contact with the inside of the first layer, is a layer formed by a composition (II) containing a fluorine-containing reactive silane compound (II) and having a surface, of which an angle of contact with water is at least 1000°; and the third layer in contact with the inside of the second layer, is a layer formed by a composition (III) containing a no fluorine-containing reactive silane compound (III).

35. A process for producing the surface-treated substrate as defined in claim 33, which comprises a step of treating the surface of a substrate with the composition (III) to form the third layer, a step of then treating the surface of the third layer with the composition (II) to form the second layer, a step of further treating the surface of the second layer with the water repellent composition as defined claim 26 to form the outermost layer, and a step of finally drying at room temperature.

36. A process for producing the surface-treated substrate as defined in claim 34, which comprises a step of treating the surface of a substrate with the composition (III) to form the third layer, a step of then treating the surface of the third layer with the composition (II) to form the second layer, a step of further treating the surface of the second layer with the water repellent composition as defined in claim 27 to form the outermost layer, and a step of finally drying at room temperature.

37. An equipment for transports, which comprises the surface-treated substrate as defined in claim 31.

38. An equipment for transports, which comprises the surface-treated substrate as defined in claim 32.

* * * * *